United States Patent [19]

Miller et al.

[11] Patent Number: 6,008,404
[45] Date of Patent: Dec. 28, 1999

[54] ACRYLATE MONOMER PREPARATION USING ALKALI METAL ALKOXIDES AS ESTER INTERCHANGE CATALYSTS AND BROMIDE SALT POLYMERIZATION INHIBITORS

[75] Inventors: Timothy M. Miller, East Brunswick; Narayanan Pondicherry, North Brunswick; Louis E. Trapasso, West Long Branch; Aaron van de Sande, Ocean, all of N.J.

[73] Assignee: Ciba Specialty Chemicals Corporation, Tarrytown, N.Y.

[21] Appl. No.: 09/132,607

[22] Filed: Aug. 11, 1998

Related U.S. Application Data

[60] Provisional application No. 60/655,449, Aug. 11, 1997.

[51] Int. Cl.$^6$ .............................. C07C 67/02; C08F 20/10
[52] U.S. Cl. ..................... 560/217; 526/173; 526/174; 526/328; 526/328.5; 560/205; 560/234
[58] Field of Search ................... 526/174, 328.5, 526/328, 173; 560/217, 234, 205

[56] References Cited

U.S. PATENT DOCUMENTS

| | | | |
|---|---|---|---|
| 4,056,580 | 11/1977 | Lochmann et al. | 526/174 |
| 4,139,690 | 2/1979 | Torigoe | 526/174 |
| 4,767,824 | 8/1988 | Ouhadi et al. | 526/174 |
| 5,037,912 | 8/1991 | Patterson et al. | 526/174 |
| 5,424,420 | 6/1995 | Hasenhuettl et al. | 536/115 |
| 5,498,751 | 3/1996 | Trapasso et al. | 560/217 |
| 5,554,785 | 9/1996 | Trapasso et al. | 560/201 |
| 5,606,103 | 2/1997 | Trapasso et al. | 560/217 |

FOREIGN PATENT DOCUMENTS

| | | | |
|---|---|---|---|
| 2455717 | 5/1975 | Germany | 526/174 |

OTHER PUBLICATIONS

Journal of Polymer Science vol. 7, 449–460 Hsieh et al, 1969.

*Primary Examiner*—Fred Zitomer
*Attorney, Agent, or Firm*—David R. Crichton

[57] ABSTRACT

The present invention relates to a process to prepare alkyl (meth)acrylate esters from corresponding alkyl/methacrylate esters using an alkali metal alkoxide as an ester interchange catalyst to produce an alkyl (meth)acrylate ester monomer product C

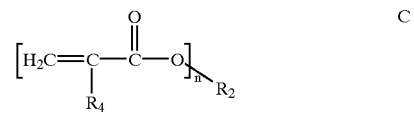

The present invention further relates to the use of bromide and iodide salts as free radical polymerization inhibitors. The present invention further relates to the use of a noninterfering alcohol or polyol that prevents anionic polymerization reactions of reactant ester B and/or alkyl (meth) acrylate product C. The present invention further relates to a process for inhibiting polymerization of (meth)acrylates being synthesized in a transesterification or ester-ester interchange reaction system.

13 Claims, No Drawings

ACRYLATE MONOMER PREPARATION USING ALKALI METAL ALKOXIDES AS ESTER INTERCHANGE CATALYSTS AND BROMIDE SALT POLYMERIZATION INHIBITORS

This application claims the benefit under 35 U.S.C. 119(e) of U.S. Provisional Application No. 60/655,449, filed Aug. 11, 1997.

SUMMARY OF THE INVENTION

The present invention relates to a process to prepare alkyl (meth)acrylate esters from corresponding alkyl/methacrylate esters using an alkali metal alkoxide as an ester interchange catalyst. Lithium methoxide or lithium t-butoxide, for example, catalyzes rapid formation of methacrylate esters, such as isobornyl methacrylate, hexyl methacrylate, and glycerol trimethacrylate, from their acetate esters in high yields with high selectivity. The present invention further relates to the use of polymerization inhibitors, LiBr, $MgBr_2$ and bromide salts of related metals or counterions. Bromide salts are useful as process polymerization inhibitors in the preparation of methacrylate or acrylate esters from alcohols by transesterification or methacrylate esters from alkyl acetates by ester interchange. The bromide salts disclosed herein can be used to prevent polymerization of the starting methyl (meth)acrylate or other lower esters of (meth)acrylic acid in the reactor or distillation column.

BACKGROUND OF THE INVENTION

Methacrylate or acrylate monomers are generally made by direct esterification of an alcohol or polyol with methacrylic acid or acrylic acid, or by transesterification of an alcohol or polyol with a lower ester of (meth)acrylic acid such as methyl methacrylate or ethyl acrylate. In such a process, a reactor is charged with the alcohol along with the desired (meth)acrylate reactant and a suitable catalyst. For instance, dodecanol is converted into dodecyl methacrylate with methacrylic acid and methane sulfonic acid. The reaction mixture is heated and the water produced as a byproduct in the process is removed as its azeotrope with a hydrocarbon solvent such as heptane. In the case of transesterification, an alcohol and methyl acrylate are heated in the presence of a tetraalkyl titanate, for instance, and the reaction is driven by removal of the byproduct, methanol. These reactions are widely practiced in industry using a large variety of specific catalysts, reaction conditions and equipment optimized for the particular monomers being manufactured. Ester interchange reactions are also well-known, particularly for the randomization of fats and oils. The use of alkali metal alkoxides is known for ester interchange reactions for fats and oils. See also U.S. Pat. No. 5,424,420, which discloses a method for preparing saccharide polyesters by transesterification using an alkali metal alkoxide.

Isobornyl methacrylate is a common monomer having utility because of the high glass transition temperature of its (co)polymers. It is conventionally prepared by acid catalyzed addition of methacrylic acid to camphene. This reaction proceeds, in the presence of an appropriate catalyst, rapidly and cleanly but to low conversion because it is an equilibrium reaction which cannot be driven by removal of a product. Thus, the acidic catalyst must be neutralized and the camphene and methacrylic acid separated from the product. Methacrylic acid is frequently lost in this separation and the camphene is a highly undesirable (because of its odor) impurity in the product. There is an obvious need for a new reaction scheme which avoids the complications of an equilibrium reaction which cannot be driven to high conversion and an offensive impurity. Another approach to preparing isobornyl methacrylate involves transesterification of isoborneol with methyl methacrylate; however, isoborneol is an extremely high melting "cakey" solid that is difficult to handle on an industrial scale.

A desirable methacrylate monomer is glycerol trimethacrylate, which is a trifunctional monomer having a low mass alcohol and a short distance between methacrylate moieties. Due to steric congestion surrounding the secondary alcohol and its ease of elimination, industrial syntheses of glycerol trimethacrylate have been impractical using conventional reaction sequences.

Typical polymerization inhibitors are phenolic compounds such as hydroquinone, 4-methoxyphenol, pyrogallol, or hindered phenolics such as butylatedhydroxytoluene and its derivatives. The oxygen in air serves as the initial radical chain stopper in these reactions since it reacts at diffusion controlled rates with carbon centered radicals which propagate chains in free radical polymerizations. The oxygen combines with the carbon centered radical to produce a much longer lived peroxy radical. The peroxy radical oxidizes a phenolic inhibitor and chain reactions are halted. Other classes of inhibitors include metal ions such as Cu(II), aromatic nitro compounds, nitrous oxide, nitroxyl compounds, aromatic amines, and aromatic heterocycles such as phenothiazine (PTZ). Some of these require air to function effectively and others do not. Some have great utility for some classes of monomers and others are not particularly useful for that class. The utility of some process inhibitors for a given class of monomers is even found to depend upon the reaction conditions being used for their preparation. For instance, phenolic inhibitors such as hydroquinone are particularly useful for preparation of (meth)acrylate esters by acid catalyzed direct esterification. Hydroquinone is a poor inhibitor for base catalyzed transesterifications because it rapidly oxidizes under basic conditions in the presence of air yielding dark reactions mixtures.

Polymerization inhibitors generally must be removed or diminished substantially in concentration before the product can be sold or polymerized by the end user. The high levels of inhibitor required to prevent polymerization during manufacture prevent effective polymerization. In the case of volatile monomers, such as allyl methacrylate, dimethylaminoethylmethacrylate, hexyl acrylate, or methyl acrylate, polymerization inhibitors can be removed via fractional distillation. Most inhibitors have significantly higher boiling points than distillable monomers and separation can be obtained. On the other hand, polymerization inhibitors cannot be removed from involatile monomers such as isodecyl acrylate, lauryl methacrylate, stearyl methacrylate, trimethylolpropane triacrylate and the like by distillation. Here, polymerization inhibitors must be removed via washing for example by removing a phenolic inhibitor with aqueous sodium hydroxide. In some cases it is undesirable to remove inhibitors via washing because of yield losses, miscibility, process complexity, or the desire for waste minimization. In other cases, low volatility of the monomer makes it difficult to remove low levels of a powerful inhibitor such as PTZ by distillation. Manufacturers of monomers are always interested in inhibitors which permit monomer process chemistry to proceed without polymerization while allowing easy separation of the product and inhibitor.

The present invention described hereinafter provides a novel reaction for the formation of alkyl (meth)acrylate monomers and fulfills the need in the field for the manufacture of such monomers using easily removed polymerization inhibitors.

SUMMARY OF THE INVENTION

The present invention relates to a process for the synthesis of (meth)acrylate monomers comprising the steps of: a) combining a reaction mixture comprising
i) a reactant ester A;

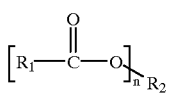

A ii) a reactant ester B;

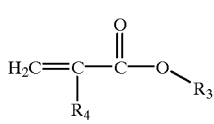

B iii) a catalytically effective amount of an alkali metal alkoxide;
iv) and optionally a polymerization inhibitor under sufficient heat to produce an alkyl (alkyl)acrylate ester monomer product C

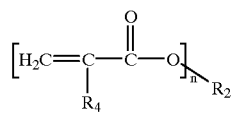

C and byproduct D

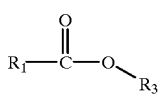

D $R_1$ is $C_1$–$C_6$ alkyl, $C_6$–$C_{10}$ cycloaliphatic or an aromatic ring which cyclic groups are unsubstituted or substituted with $C_1$–$C_4$ alkyl or hydroxyl, preferably $R_1$ is $C_1$–$C_4$ alkyl or cyclohexyl or a benzene ring, more preferably $R_1$ is $C_1$–$C_2$ alkyl. $R_2$ is a derivative of an alcohol or polyol $R_2(OH)_n$ selected from n- or iso-alkanols having 2 to 20 carbon atoms, furfuryl alcohol, tetrahyrofurfuryl alcohol, benzyl alcohol, 2-phenoxyethanol, cyclohexanol, allyl alcohol, methallyl alcohol, butenol, ethylene glycol, triethylene glycol, 1,3-butanediol, trimethyol propane, pentaerythritol, dipentaerythritol, 2,2-dimethyl-1,3-propandiol, glycerol, bornyl alcohol, borneol, isobornyl alcohol, ethoxyethanol, butoxyethanol, propoxyethanol and higher ethoxylates, and alkamines and di(alk) aminoalcohols wherein alk is methyl, ethyl, propyl or butyl, and n is an integer from 1 to 4, corresponding to the number of hydroxyl groups on alcohol or polyol $R_2(OH)_n$. $R_3$ is $C_1$–$C_2$ alkyl and $R_4$ is hydrogen or methyl. Most preferably, $R_1$, $R_3$ and $R_4$ are methyl.

Byproduct D can be removed to drive the reaction to completion and/or the alkyl (meth)acrylate product C can be quenched with an acid and product C recovered via reduced pressure distillation. Alternatively, alkyl (meth)acrylate product C can be washed with an aqueous solution to remove residual alkali metal alkoxide and polymerization inhibitor, if present.

The alkali metal alkoxide is advantageously selected from the group consisting of lithium methoxide, lithium ethoxide, lithium butoxide, lithium t-butoxide, lithium isopropoxide and mixtures thereof, more preferably lithium methoxide or lithium t-butoxide or mixtures thereof.

In a particularly preferred embodiment, the reaction mixture further comprises at least one process free radical polymerization inhibitor. The process free radical polymerization inhibitor can be selected from propyl gallate, thiodiphenol, methoxyphenol, phenylnaphtyl amine, a bromide salt and mixtures thereof. More preferably, at least one process polymerization inhibitor is a bromide or iodide salt, particularly lithium bromide, magnesium bromide, sodium bromide, cesium bromide, potassium bromide, calcium bromide, rubidium bromide, strontium bromide, barium bromide, tetraalkylammonium bromide and phosphonium bromide, most preferably lithium bromide, magnesium bromide and sodium bromide.

In a still further embodiment, the reaction mixture further comprises a noninterfering alcohol or polyol that prevents anionic polymerization reactions of reactant ester B and/or alkyl (meth)acrylate product C. The noninterfering alcohol can be selected from t-butanol, borneol or isoborneol.

The present invention further relates to a process for inhibiting polymerization of (meth)acrylates being synthesized in a transesterification reaction system comprising:
a) providing a (meth)acrylate producing reaction mixture comprising
i) an alcohol or polyol;
ii) an ester of a (meth)acrylate;
b) reacting said reaction mixture in the presence of a catalyst and a bromide salt to produce an alcohol or polyol ester of said (meth)acrylate substantially free of polymeric derivatives of said reaction mixture and resulting product. The bromide salt can be selected from lithium bromide, magnesium bromide, sodium bromide, cesium bromide, potassium bromide, calcium bromide, rubidium bromide, strontium bromide, barium bromide, tetraalkylammonium bromide and phosphonium bromide, preferably lithium bromide, magnesium bromide and sodium bromide.

The present invention further relates to a process for inhibiting polymerization of acrylates being synthesized in an ester interchange reaction system comprising:
a) providing an acrylate producing reaction mixture comprising
i) a first ester; and
ii) a second ester containing at least unsaturated group;
b) reacting said reaction mixture in the presence of a catalyst and a bromide salt to produce an alkyl (meth) acrylate substantially free of polymeric derivatives of said reaction mixture and resulting product. The bromide salt can be selected from lithium bromide, magnesium bromide, sodium bromide, cesium bromide, potassium bromide, calcium bromide, rubidium bromide, strontium bromide, barium bromide, tetraalkylammonium bromide and phosphonium bromide, preferably lithium bromide, magnesium bromide and sodium bromide. The catalyst can preferably be an alkali metal alkoxide advantageously selected from the group consisting of lithium methoxide, lithium ethoxide, lithium butoxide, lithium t-butoxide, lithium isopropoxide and mixtures thereof, most preferably lithium methoxide or lithium t-butoxide or mixtures thereof.

DETAILED DESCRIPTION OF THE INVENTION

The present invention relates to a novel reaction for the preparation of methacrylate monomers. In this reaction, a first ester, usually an alkyl acetate, is converted into the desired alkyl (meth)acrylate ester monomer directly without isolation of the intermediate alcohol via an ester interchange reaction. Formation of (meth)acrylate esters is significantly more difficult than formation of aromatic or saturated carboxylic acid esters because of intervention of side reactions arising from the dimerization of acrylic acid and Michael addition of alcohol across the olefinic double bond in the (meth)acrylate moiety. Surprisingly, Applicants discovered that the addition of strongly basic catalysts, such as alkali metal alkoxides, catalyze ester interchange reactions of alkyl esters with alkyl (meth)acrylates very rapidly and cleanly.

Reaction: The ester interchange reaction described herein provides a means for preparing an alkyl (alkyl)acrylate monomer whereby a lower acyl ester and an alkyl ester derived from an unsaturated carboxylic acid are reacted under essentially anhydrous conditions in the presence of an alkali metal alkoxide catalyst and a polymerization inhibitor at an elevated temperature. The reaction sequence can be represented by the following reaction sequence:

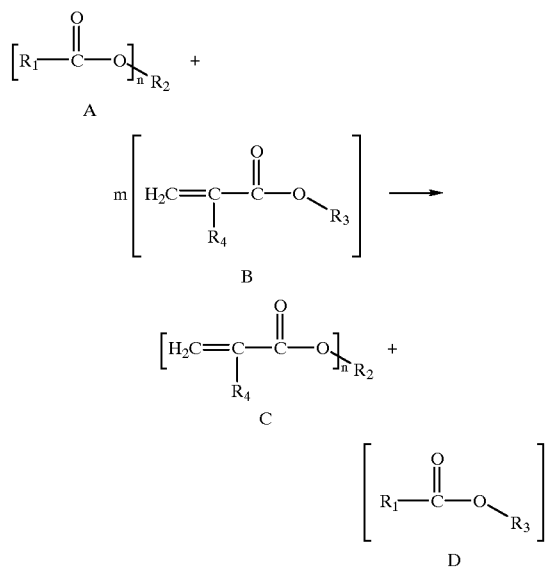

wherein reactant esters A and B react in the presence of a selected basic catalyst to produce an alkyl (meth)acrylate ester monomer product C and byproduct D, which is removed to drive the reaction to completion. The variable "m" can be varied from 1 to 5 depending on the number of hydroxyl groups and whether excess reactants are used. The reaction is preferably conducted in the absence of water, which promotes rapid and complete conversion, by azeotropic drying.

Reactant ester A is an ester wherein $R_1$ is $C_1$–$C_6$alkyl, $C_6$–$C_{10}$ cycloaliphatic or an aromatic ring which cyclic groups are unsubstituted or substituted with $C_1$–$C_4$alkyl or hydroxyl, preferably $C_1$–$C_4$ alkyl or cyclohexyl or benzene ring, still more preferably $C_1$–$C_2$alkyl, and most preferably methyl. $R_2$ is derived from the reaction of an alcohol or polyol $R_2(OH)_n$ selected from n- or iso- 2 to 20 carbon atom alkanols, furfuryl alcohol, tetrahyrofurfuryl alcohol, benzyl alcohol, 2-phenoxy-ethanol, cyclohexanol, allyl alcohol, methallyl alcohol, butenol, ethylene glycol, triethylene glycol, 1,3-butanediol, trimethyol propane, pentaerythritol, dipentaerythritol, 2,2-dimethyl-1,3-propandiol, glycerine, bornyl alcohol, borneol, isobornyl alcohol, ethoxyethanol, butoxyethanol, propoxyethanol, and higher ethoxylates, such as ethoxybutanol, ethoxypropanol, and alkamines, particularly di(alk)aminoalcohols wherein alk is methyl, ethyl, propyl or butyl, such as N,N-dimethylamino ethanol, N,N-diethylamino ethanol, N,N-dipropylamino ethanol, N,N-dibutylamino ethanol and n is an integer from 1 to 4, corresponding to the number of hydroxyl groups on alcohol or polyol $R_2(OH)_n$.

Reactant ester B is a lower acyl ester of methacrylic acid, particularly methyl or ethyl methacrylate wherein $R_3$ is a $C_1$–$C_2$alkyl group, most preferably methyl, and $R_4$ is $C_1$–$C_3$alkyl, more preferably methyl or ethyl, most preferably methyl. Reactant ester B can be prepared in known fashion via acid catalyzed reaction of an alcohol and a methacrylic acid.

In one embodiment of the invention, reactant esters A and B and the alkali metal alkoxide are mixed in a reaction vessel and then heated to a reaction temperature (about 80 to 120° C.). As the reaction proceeds, the byproduct ester is removed to drive the reaction to completion. Preferably, the by-product ester is removed by distillation or azeotropic distillation. The reactants proceed via an ester-ester interchange reaction to produce the desired alkyl (meth)acrylate monomer. The molar ratio of the reactants can be varied over a wide range. Preferably, the amounts of reactant materials A and B are adjusted so that the molar ratio of the ester groups of reactant material A is about equal to the available ester groups of reactant material B. A reaction temperature is selected at which the reactant materials A and B are liquid. The selection of an appropriate reaction temperature is a matter that can be readily determined by one of ordinary skill in the art without undue experimentation. In order to secure the benefits of this invention, the reaction must be conducted in the presence of a strongly basic catalyst, such as an alkali metal alkoxide.

The catalysts employed in the present invention are alkali metal alkoxides. The lithium alkoxides are generally preferred. Preferred catalysts include lithium methoxide, lithium ethoxide, lithium butoxide, lithium t-butoxide, lithium isopropoxide and mixtures thereof. Lithium methoxide and lithium t-butoxide are generally most preferred in the practice of the present invention. Lithium t-butoxide is commercially available in bulk from Chemetall GmbH, Frankfurt am Main, Germany and has good solubility (10%) in inert hydrocarbon solvents such as cyclohexane. The catalyst is generally used in an amount less than about 5 mole % (based on reactant A), preferably in the range of about 1 to 2.5 mole %.

In a more preferred embodiment, reactant ester A is mixed with reactant ester B and at least one polymerization inhibitor at an elevated temperature to produce a mixture of reactant esters A and B. The mixture is then combined with the alkali metal alkoxide and brought to reflux. The byproduct ester is removed to drive the reaction to completion.

Applicants have discovered that the addition of t-butanol or, in the case of isobornyl acetate, the addition of isoborneol prevents anionic polymerization reactions during the ester-ester interchange. An additional free radical polymerization inhibitor is preferably added to the reaction mixture as well. The additional polymerization inhibitor can be selected from any number of the well-known inhibitors, such as propyl gallate, thiodiphenol, methoxyphenol, phenylnaphtyl amine, though the best results have been obtained by using the novel inhibitors discussed more fully below.

Preferred Embodiments for the Ester-Ester Interchange: Preferred starting esters are acetates of the desired alcohol such as isobornyl acetate or n-hexyl acetate. The methacryloyl moiety is preferably supplied by methyl or ethyl methacrylate. In the synthesis of isobornyl methacrylate by ester interchange, isobornyl acetate and methyl methacrylate are charged to a reactor. The reaction is driven to high conversion by removal of the byproduct methyl acetate. The preferred catalyst is a lithium alkoxide, particularly lithium t-butoxide. The reaction mixtures must be free of water for rapid and complete conversion which is usually accomplished by azeotropic drying using a hydrocarbon solvent. The preferred noninterfering alcohol or polyol is t-butanol or, in the preparation of isobornyl acetate, isoborneol.

The present invention further relates to a method for inhibiting the polymerization of monomers produced in accordance with conventional synthesis routes or via the reaction sequence described above. In order to prevent polymerization of the (meth)acrylic acid during the reaction, the reactants are nearly always combined in the presence of air and one or more polymerization inhibitors. The polymerization inhibitors, in combination with air, function to prevent polymerization of the reactant or product monomers. Polymerization inhibitors are usually present in both the reaction mixture and its product stream to prevent process polymerization reactions and the final product as sold to prevent polymerization during storage. The polymerization inhibitors used in the reactor or recovery steps ("process polymerization inhibitors") must generally be more active than a final product inhibitor due to the high temperatures encountered during manufacture and recovery of the final product.

The transesterification reaction is a well-known process wherein an alcohol and an ester are the starting materials. For instance, in the synthesis of ethyleneglycol dimethacrylate by transesterification, ethyleneglycol and methyl methacrylate are charged to the reactor. A tin compound can be used as described in U.S. Pat. Nos. 5,498,751, 5,554,785 and 5,606,103, which are incorporated herein by reference, or a combination of a tin compound and sodium carbonate as the catalyst. In order to prevent metal ion exchange with the sodium carbonate and because sodium bromide has adequate solubility in ethyleneglycol, sodium bromide is used as the inhibitor in combination with methyl hydroquinone.

A novel class of process polymerization inhibitors are bromide salts, such as lithium, magnesium, or sodium bromide which meet all of the requirements for a process inhibitor. Said polymerization inhibitors prevent free radical chain polymerization of the ester product and ester reactants under monomer synthesis conditions, have good solubilities in the organic reaction medium encountered in a monomer synthetic reaction, and are easily removed via distillation due to their complete nonvolatility relative to organic monomers or via aqueous water washing.

Particularly preferred bromide salts which have been found useful as polymerization inhibitors in laboratory, pilot plant, or commercial scale manufacture include lithium bromide, magnesium bromide, and sodium bromide. Other bromide salts that can be used are cesium, potassium, calcium, rubidium, strontium, barium, and tetraalkylammonium or phosphonium. Chloride salts are not sufficiently effective. Iodide salts, while capable of inhibiting polymerization, are less practical due to the formation of dark reaction mixtures, which may be due to the formation of molecular iodine caused by air oxidation of iodide.

Bromide ion is not typically held by those skilled in the art to have polymerization inhibitory capability. While not wishing to be bound by a particular theory or mechanism of action, the inhibitory power of bromide salts may be rationalized by the facile reaction of bromide ion with a peroxy radical produced from the reaction of a carbon centered radical and molecular oxygen. Carbon centered radicals are the chain propagating species in radical polymerizations of vinylic monomers. The function of an inhibition system in the manufacture of a monomer is to prevent chain reaction ie. addition of a carbon centered radical to a monomer molecule regenerating a higher molecular weight carbon centered radical. Reaction of a peroxy radical and bromide ion is believed to produce an alkylperoxy anion and a bromine radical. Alkylperoxy anions are relatively unreactive and likely remain unchanged. Bromine radicals may combine to produce molecular bromine which volatilizes or are dissipated by other reactions. The observation that the effectiveness of halides as inhibitors has the trend $I^-\cong Br^- >> Cl^- > F^-$ correlates with their oxidation potentials. Inhibitory power is not easy to assess and can be dependent on the monomer(s) in question, temperature, oxygen concentration, and the concentration and identities of other components present in the reaction mixture.

Applicants have found that bromide salts are particularly useful as inhibitors in the syntheses of (meth)acrylate monomers by both ester interchange or transesterifications reactions. Applicants have further found that lithium bromide is an effective polymerization inhibitor during the lithium t-butoxide catalyzed ester interchange reactions of isobornyl acetate, n-hexyl acetate, and glycerol triacetate (triacetin) with methyl methacrylate.

The resulting products, whether synthesized by ester-ester interchange or transesterification, are freed of catalyst and inhibitor using vacuum distillation or aqueous washing. Due to the involatile nature of the reaction catalyst, a very high level of product can be recovered in the vapor phase of the distillation column. Yields following recovery via distillation are obtained in excess of 70%, more preferably in excess of 85%. For some monomer products, the theoretical yield is in excess of 90%. Purity levels of the recovered products are generally in excess of 92%, more preferably in excess of 97%. Purity of methacrylate or acrylate monomers is assessed using gas chromatography. The gas chromatograph is equipped with a capillary column and flame ionization detector. A typical capillary column suitable for these analyses is a 30-meter Rtx-1 column (available from Restek Corporation, Bellefonte, Pa.) having a 0.5 micron film thickness. The sample is injected neat into the injection port and the area under the peak(s) attributable to the monomer is divided by the total area of all of the peaks in the chromatogram. The ratio corresponds to the purity of the monomer sample.

The present invention is described more fully with reference to the following non-limiting examples.

Example 1

Isobornyl Methacrylate (IBOMA) Prepared with Lithium Bromide

A 3-L 4-necked round-bottomed flask equipped with a mechanical stirrer, air sparge (10–15 mL/min), thermocouple, 12-inch column (packed with 0.20 inch Propak packing, approximately 6 plates), and variable reflux head is charged with 588 g (3 moles) of isobornyl acetate. The head is fitted with a plastic tube permitting the feeding of a 2% lithium bromide solution in methyl methacrylate at the rate of 1.9 mL/hr as a down column inhibitor. Lithium bromide (3.0 g, 0.03 moles), t-butanol (22.5 g, 0.304) cyclohexane (300 g), and methyl methacrylate (450 g, 4.5 moles) are added. The reaction mixture is brought to reflux and about 10 mL of cyclohexane/$H_2O$ is distilled out over approximately 15 minutes. A solution of 10% lithium t-butoxide in cyclohexane (40 g, 0.05 moles) is added and the reaction placed under total reflux until the head temperature drops to 57° C. The cyclohexane/methyl acetate azeotrope is removed at a reflux ratio of 9:1. The head temperature remains at 57° C. for the first two-thirds of the reaction and then slowly rises to 70° C. at the conclusion while the pot temperature rises to about 105–110° C. The reaction is continued until the ratio of isobornyl methacrylate to isobornyl acetate exceeded 100. Once the reaction is complete, the batch is cooled to 80° C. and acetic acid (5.4 g, 0.09 moles) is added. The remaining cyclohexane and MMA are removed via vacuum distillation (70–80° C.) and the crude product is distilled using a one-plate distillation apparatus. A 2-L two-necked round-bottomed flask equipped with a mechanical stirrer, Claisen head, downward condenser, and receiver is charged with 680 g of crude stripped IBOMA and 3 10 g of Irganox 1010. The apparatus is evacuated to 2–5 mm of Hg and the IBOMA distills rapidly (2 hour) at 95–100° C. The yield of crude IBOMA is 680 g (102%). After distillation, the yield is 650 g (97.5%) and the heel (19 g) is about 2.8% of the charge. The IBOMA produced in this reaction is 99.1% pure and the major impurity is isobornyl acetate.

Example 2

Isobornyl Methacrylate Isolated by Washing

The crude reaction is run as described in Example 1. Isobornyl methacrylate is freed of lithium bromide and lithium acetate by washing rather than distillation. The crude isobornyl methacrylate is diluted with an equal weight of cyclohexane and the product washed with 20% by weight of 20% caustic. Rapid and complete separation of the two phases occurs. The organic phase is washed with 20% by weight of brine (15% NaCl containing 2% $NaHCO_3$) and the phases separate cleanly and rapidly. The cyclohexane is removed via distillation under vacuum yielding 665 g of IBOMA.

Comparative Example 1

Isobornyl Methacrylate without Lithium Bromide

A 3-L 4-necked round-bottomed flask equipped with a mechanical stirrer, air sparge (10–15 mL/min), thermocouple, 12-inch column (packed with 0.20 inch Pro-pak packing, approximately 6 plates), and variable reflux head is charged with 588 g (3 moles) of isobornyl acetate, cyclohexane (300 g), and methyl methacrylate (450 g, 4.5 moles). The reaction mixture is brought to reflux and about 10 mL of cyclohexane/$H_2O$ is distilled out over approximately 15 minutes. A solution of 10% lithium t-butoxide in cyclohexane (40 g, 0.05 moles) is added and the reaction placed under total reflux until the head temperature drops to 57° C. The cyclohexane/methyl acetate azeotrope is removed at a reflux ratio of 9:1. The head temperature remains at 57° C. for the first two-thirds of the reaction and then slowly rises to 70° C. at the conclusion while the pot temperature rises to about 105–110° C. The reaction is continued until the ratio of isobornyl methacrylate to isobornyl acetate exceeds 100. Once the reaction is complete, the batch is cooled to 80° C. and acetic acid (5.4 g, 0.09 moles) is added. The remaining cyclohexane and methyl methacrylate are removed via vacuum distillation (70–80° C.). When the crude product is dissolved in (2/98 vol/vol) in methanol, a cloudy white precipitate forms. The crude product is diluted with an equal weight of cyclohexane and washed with 20% by weight of 20% caustic. The two phases do not separate on prolonged standing. This result as well as the large quantity of precipitate produced on dissolving the crude reaction mixture in methanol indicate the presence of polymer in the reaction mixture.

Example 3

Isobornyl Methacrylate with Magnesium Bromide

A 3-L 4-necked round-bottomed flask equipped with a mechanical stirrer, air sparge (10–15 mL/min), thermocouple, 12-inch column (packed with 0.20 inch Pro-pak packing, approximately 6 plates), and variable reflux head is charged with 196 g (1 mole) of isobornyl acetate. Magnesium bromide (1 g, 0.005 moles), isoborneol (7.71 g, 0.05 moles) cyclohexane (100 g), and methyl methacrylate (150 g, 1.5 moles) are added. The reaction mixture is brought to reflux and about 10 mL of cyclohexane/$H_2O$ is distilled out over approximately 15 minutes. A solution of 10% lithium t-butoxide in cyclohexane (15.8 g, 0.02 moles) is added. The reaction mixture is placed under total reflux until the head temperature drops to 57° C. The cyclohexane/methyl acetate azeotrope is removed at a reflux ratio of 4:1. The head temperature remains at 56° C. for the first two-thirds of the reaction and then slowly rises to 78° C. at the conclusion, while the pot temperature rises to about 105° C. The reaction is continued until the ratio of isobornyl methacrylate to isobornyl acetate exceeds 100. Once the reaction is complete, the batch is cooled to 80° C. and acetic acid (1.8 g, 0.03 moles) is added. The remaining cyclohexane and methyl methacrylate are removed via vacuum distillation (70–80° C.) and the crude product is distilled using a one-plate distillation apparatus. A 1-L two-necked round-bottomed flask equipped with a mechanical stirrer, Claisen head, downward condenser, and receiver is charged with 230 g of crude stripped IBOMA and 1.5 g of Irganox 1010. The apparatus is evacuated to 2–5 mm of Hg and the IBOMA distills rapidly (2 hour) at 95–100° C. The yield of crude IBOMA is 230 g (103.5%). After distillation, the yield is 201 g (90.5%) and the heel (18.6 g) is about 4% of the charge.

Example 4

Glycerol Trimethacrylate

A 3-L 4-necked round-bottomed flask equipped with a mechanical stirrer, air sparge (10–15 mL/min), thermocouple, 12-inch column (packed with 0.20 inch Pro-pak packing, approximately 6 plates), and variable reflux head is charged with 218 g (1 mole) of glycerol triacetate. Lithium bromide (4 g, 0.046 moles), cyclohexane (300 g), and methyl methacrylate (450 g, 4.5 moles) are added. The reaction mixture is brought to reflux and about 10 mL of cyclohexane/$H_2O$ is distilled out over approximately 15 minutes. A solution of 10% lithium t-butoxide in cyclohexane (39.5 g, 0.05 moles) is added. The reaction is placed under total reflux until the head temperature drops to 62° C. The cyclohexane/methyl acetate azeotrope is removed at a reflux ratio of 9:1. The head temperature remains at 62° C.

for the first two-thirds of the reaction and then slowly rises to 81° C. at the conclusion, while the pot temperature rises to about 92° C. The reaction is continued until the ratio of glycerol trimethacrylate to glycerol dimethacrylate acetate exceeds 100. Once the reaction is complete, cyclohexane and MMA are removed via vacuum distillation (70–80° C.). The weight of the crude after reaction is 285 g. The crude is reconstituted with equal volumes of cylcohexane and washed twice with 114 g of 20% caustic solution. Separations of the aqueous and organic phases are sharp and rapid indicating little if any polymeric material in the reaction mixture. The organic layer is washed with 114 g of 0.5N HCl solution to remove color. Finally the crude is washed with 114 g of brine solution. The crude is then stripped under reduced vacuum (20 mm Hg) to yield final product (243 g) corresponding to a yield of 82%. The purity of the glycerol trimethacryate is 99.2%.

Comparative Example 2

Glycerol Trimethacrylate in the Absence of Lithium Bromide

A 3-L 4-necked round-bottomed flask equipped with a mechanical stirrer, air sparge (10–15 mL/min), thermocouple, 12-inch column (packed with 0.20 inch Propak packing, approximately 6 plates), and variable reflux head is charged with 218 g (1 mole) of glycerol triacetate, cyclohexane (300 g), and methyl methacrylate (450 g, 4.5 moles) are added. The reaction mixture is brought to reflux and about 10 mL of cyclohexane/$H_2O$ is distilled out over approximately 15 minutes. A solution of 10% lithium t-butoxide in cyclohexane (39.5 g, 0.05 moles) is added and the reaction is placed under total reflux until the head temperature drops to 62° C. The cyclohexane/methyl acetate azeotrope is removed at a reflux ratio of 9:1. The head temperature remains at 62° C. for the first two-thirds of the reaction and then slowly rises to 81° C. at the conclusion, while the pot temperature rises to about 92° C. The reaction is continued until the ratio of glycerol trimethacrylate to glycerol dimethacrylate acetate exceeds 100. Once the reaction is complete, cyclohexane and methyl methacrylate are removed via vacuum distillation (70–80° C.). Weight of the crude after reaction is 290 g. The crude is reconstituted with equal volumes of cyclohexane and washed with 114 g of 20% caustic solution. The caustic solution separates slowly and incompletely from the organic phase indicating polymeric material in the reaction mixture. A long settling time is required for a complete separation to occur. The second caustic wash is clean. The organic layer is washed with 114 g of 0.5N HCl solution to remove color. Finally the crude is washed with 114 g of brine solution. The crude is then stripped under reduced vacuum (20 mm Hg) to yield final product (213 g) corresponding to a yield of 82%. The polymer (NTU) of the final product is 300.

Example 5

Ethylene Glycol Dimethacrylate (EGDMA)

A 3-L round-bottomed, 4-necked flask is fitted with a 1-ft. fractionating column, variable reflux distillation head, air sparge tube, and a side arm containing a mercury thermometer and addition funnel. The air sparge rate is set to 30 mL/min. The flask is charged with ethylene glycol (310 g, 5 moles), methyl methacrylate (1200 g, 12 moles), cyclohexane (80 g, 1 mole), 73% dimethyltin dichloride in methanol (15 g, 0.05 moles), 25% sodium methoxide in methanol (10.8 g, 0.05 moles), 5.3 g (0.05 moles) of sodium carbonate, 8 g of MEHQ and 8 g of sodium bromide. The cyclohexane methanol azeotrope is removed via distillation. The methanol is removed from the overhead by washing it with water, and the cyclohexane is returned to the flask. The reaction is continued until the ratio of EGDMA to hydroxyethyl methacrylate exceeds 50:1. The excess methyl methacrylate and cyclohexane are removed via distillation, and the crude EGDMA is diluted with an equal weight of cyclohexane. The organic solution is washed twice with 20% of its weight of 20% caustic followed by brine. The separations of the organic and aqueous phases are in all cases rapid and sharp indicating the absence of polymer. The cyclohexane is removed from the product by distillation yielding 920 g (93%) of EGDMA.

Example 5

Hexyl Acrylate

A 4-necked 3-liter round-bottomed flask equipped with a mechanical stirrer and a Teflon paddle, 12-inch column (packed with 0.20 inch Propak packing, approximately 6 plates) fitted with a variable take-off distillation head, an air sparge tube (12 ml/min.), a side arm fitted with a 12" immersion thermometer and a 500-mL pressure equalizing dropping funnel is charged with 204 g (2 moles) of hexyl alcohol. MEHQ (0.97 g, 0.0075 moles), dibutyltin oxide (4.98 g, 0.02 moles), lithium bromide (1.5 g, 0.017 moles), heptane (50 g), and methyl acrylate (258 g, 3 moles) are added. The reaction mixture is brought to reflux and take off began at such a rate as to maintain a head temperature between 57–59° C. The reflux ratio for most part of the reaction is kept at a ratio of 4:1. The overhead is washed with approximately equal volume of water and the upper phase returned to the pot until the ratio of hexyl acrylate to hexyl alcohol exceeds 7:1. The product is then distilled under reduced pressure. When the overhead temperature corresponds to the boiling point of hexyl acrylate (88–90° C. at ~24 mm Hg) the heart cut was collected until the pot temperature reached 115° C. After distillation, the yield was 228 g (73%) and the heel (62 g) was about 11% of the charge.

Example 6

Comparison of Process Polymerization Inhibitors

Applicants studied polymer development in static reaction mixtures containing isobornyl methacrylate, methyl methacrylate, and t-butanol with 3000 ppm of various inhibitors. The reaction mixture is heated to a boil (approximately 120° C.) with an air sparge set to 50 cc/min for 1 hour. The air sparge is then turned off for 10 minutes while maintaining the mixture under reflux. After 10 minutes the air sparge is reinstated and the polymer level ascertained by measuring the nephthalometric turbidometric units (NTUs) as a 2% solution in methanol. The higher the NTUs the higher the level of the polymer in solution. Table 1 summarizes the data.

TABLE 1

| Inhibitor | NTU |
| --- | --- |
| Phenothiazene | 18 |
| Irganox 1010 | 15 |
| Thiodiphenol | 250 |
| 4-Methoxyphenol | 200 |

TABLE 1-continued

| Inhibitor | NTU |
|---|---|
| 2-Phenylnaphthyl amine | 200 |
| Benzoquinone | 0.6 |
| Hydroquinone | 0.5 |
| Lithium bromide | 3.1 |

The foregoing description of the presently preferred embodiments should be taken as illustrative, rather than as limiting, the present invention as defined by the claims. Numerous variations and combinations of the features described above can be utilized without departing from the spirit of the present invention.

We claim:

1. A process for inhibiting polymerization of (meth) acrylates being synthesized in a transesterification reaction system comprising:
   a) providing a (meth)acrylate producing reaction mixture comprising
      i) an alcohol or polyol;
      ii) an ester of a (meth)acrylate;
   b) reacting said reaction mixture in the presence of a catalyst and a bromide salt to produce an alcohol or polyol ester of said (meth)acrylate substantially free of polymeric derivatives of said reaction mixture and resulting product.

2. A process according to claim 1 wherein the bromide salt is selected from lithium bromide, magnesium bromide, sodium bromide, cesium bromide, potassium bromide, calcium bromide, rubidium bromide, strontium bromide, barium bromide, tetraalkylammonium bromide and phosphonium bromide.

3. A process according to claim 2 wherein the bromide salt is selected from lithium bromide, magnesium bromide and sodium bromide.

4. A process for inhibiting polymerization of (meth) acrylates being synthesized in an ester interchange reaction system comprising:
   a) providing a (meth)acrylate producing reaction mixture comprising
      i) a first ester; and
      ii) a second ester containing at least unsaturated group;
   b) reacting said reaction mixture in the presence of a catalyst and a bromide salt to produce an alkyl (meth) acrylate substantially free of polymeric derivatives of said reaction mixture and resulting product.

5. A process according to claim 4 wherein the bromide salt is selected from lithium bromide, magnesium bromide, sodium bromide, cesium bromide, potassium bromide, calcium bromide, rubidium bromide, strontium bromide, barium bromide, tetraalkylammonium bromide and phosphonium bromide.

6. A process according to claim 5 wherein the bromide salt is selected from lithium bromide, magnesium bromide and sodium bromide.

7. A process according to claim 4 wherein the catalyst is an alkali metal alkoxide.

8. A process according to claim 4 wherein the catalyst is selected from the group consisting of lithium methoxide, lithium ethoxide, lithium butoxide, lithium t-butoxide, lithium isopropoxide and mixtures thereof.

9. A process according to claim 8 wherein the catalyst is lithium methoxide or lithium t-butoxide or mixtures thereof.

10. A process according to claim 1 wherein the product of step b) has a monomer purity level of at least about 92% as determined by gas chromotography.

11. A process according to claim 1 wherein the product of step b) has a monomer purity level of at least about 97% as determined by gas chromotography.

12. A process according to claim 4 wherein the product of step b) has a monomer purity level of at least about 92% as determined by gas chromatography.

13. A process according to claim 1 wherein the product of step b) has a monomer purity level of at least about 97% as determined by gas chromotography.

\* \* \* \* \*